United States Patent [19]

Biella et al.

[11] Patent Number: 5,430,029
[45] Date of Patent: Jul. 4, 1995

[54] PHARMACEUTICAL COMPOSITIONS ACTIVE IN THE THERAPY OF SLEEP DISORDERS

[75] Inventors: Gabriele Biella, Pavia; Franco Fraschini, Milan; Bojidar Stankov, Milan; Luigi F. Strambi, Milan, all of Italy

[73] Assignee: Iflo-Istituto Farmacologico Lombardo S.A.S. di Giorgio e Ald. Laguzzi, Milan, Italy

[21] Appl. No.: 161,744

[22] Filed: Dec. 2, 1993

Related U.S. Application Data

[63] Continuation of Ser. No. 881,521, May 12, 1992, abandoned.

[30] Foreign Application Priority Data

May 13, 1991 [IT] Italy ............... MI91A1299

[51] Int. Cl.6 .............. A61K 31/55; A61K 31/405
[52] U.S. Cl. .................. 514/220; 514/221; 514/415; 514/923
[58] Field of Search ............ 514/220, 221, 415, 923

[56] References Cited

FOREIGN PATENT DOCUMENTS 0126630 2/1989 European Pat. Off. .
8901472 2/1989 WIPO .

OTHER PUBLICATIONS

Chemical Abstracts 85: 53744z, 1976.
Chemical Abstracts 97: 86519p, 1982.
Chemical Abstracts 100: 185660q, 1984.
Sleep, vol. 13, No. 3, Jun. 1990, pp. 232–244, Raven Press, Ltd, N.Y., US; G. Copinschi et al.
Journal of Pineal Research, vol. 7, No. 2, 1989, pp. 205–209, Alan R. Liss, Inc.; D. Sugden.
Life Sciences, vol. 40, No. 15, 17th Apr. 1987, pp. 1537–1543, Pergamon Journals Ltd., US; B. Suranyi-Cadotte.
Endocrinologia Japonica, vol. 33, No. 3, Jun. 1986, pp. 405–4±4; M. Kabuto et al.
Biochemical Pharmacology, vol. 40, No. 12, 15th Dec. 1990, pp. 2701–2705, Pergamon Press, Oxford, GB, Niles et al.

Primary Examiner—Marianne M. Cintins
Assistant Examiner—Kimberly R. Jordan
Attorney, Agent, or Firm—Hedman, Gibson & Costigan

[57] ABSTRACT

The present invention relates to new pharmaceutical compositions active in the therapy of sleep disorders comprising N-acetyl-5-methoxy-triptamine (melatonin) or one of its derivatives, preferably 2-iodo-N-acetyl-5-methoxy-triptamine (2-iodomelatonin), 2-bromo-N-acetyl-5-methoxy-triptamine (2-bromomelatonin), 2-chloro-N-acetyl-5-methoxy-triptamine (2-chloromelatonin) or 6-chloro-N-acetyl-5-methoxy-triptamine (6-chloromelatonin), at a dosage comprised between 10 and 100 mg, preferably comprised respectively between 20 and 80 mg between 10 and 20 mg and between 10 and 40 mg alone or in association with a benzodiazepinic derivative at a dosage comprised between 0.06 and 25 mg.

30 Claims, No Drawings

PHARMACEUTICAL COMPOSITIONS ACTIVE IN THE THERAPY OF SLEEP DISORDERS

This is a continuation of application Ser. No. 07/881,521, filed May 12, 1992, now abandoned.

The present invention relates to new pharmaceutical compositions active in the therapy of sleep disorders and in the pre-anaesthetic medication, comprising N-acetyl-5-methoxy-triptamine (melatonin) or one of its derivatives having general formula (I)

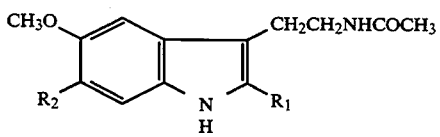

wherein $R_1$ and $R_2$, the same or different, are H or halogens, alone or in association with a benzodiazepinic derivative. Melatonin is a hormone mainly sinthesized within the pineal gland, of which it is one of the most important products. Apart the known capacity of melatonin to affect the reproductive activity in different species of mammals, the most accepted interpretation is that it is playing an essential role in the transmission of the photoperiodic information from the environment and therefore acting as a synchroniser of the endogenous biological clock.

Light is in fact the main synchroniser of the circadian and seasonal rhythms and, because of the role played by melatonin in transducing the information concerning daylength, it is accepted that it is acting as a synchroniser of the biological rythms with the day-night cycle.

Further, it is known that melatonin is controlling the sleep-wake cycle in blind people, suffering from desynchronisation of the circadian rhythm, and alleviates the problems related to rapid time zone changes (the so-called "jet-lag" which occurs following rapid transfer covering more than 5 time zones), limiting the insomnia and lethargy which follow such trips, in particular Eastward, the direction in which desynchronisation is more pronounced. Little is still known concerning the mechanism of action of melatonin; at a molecular level its capacity to suppress the stimulation in a second messenger, namely the cAMP, has been demonstrated, but its mechanism of action at the cellular level or at the level of the neuronal circuits has not been clarified yet. A description of the biologic activity of melatonin is reported by J. Arendt in Clinical Endocrinology (1988), 29, 205–229. Benzodiazepines are a broad family of drugs acting on the structures of the central nervous system (CNS) through receptors of the gamma aminobutyric acid (GABA), the most widespread inhibitory neurotransmitter in CNS; they are thought to possess qualitatively similar actions, and use the same mechanisms, whereas quantitative differences may occur.

The pharmacological properties of benzodiazepines substantially spring from their action in the central nervous system. In humans, the most evident effects are sedation, sleep induction, anxiety reduction, muscle relaxation and anticonvulsive activity. In particular all benzodiazepines express substantially similar effects on the most important sleep parameters and, with the exception of cases which require a specific therapy or nonpharmacological interventions, are considered drugs of choice for the treatment of insomnia, as they have a good therapeutical index, give rise to a smaller number of pharmacological interactions and have a low toxico-manigenic power with respect to other hypnotic drugs.

One of the drawbacks of the benzodiazepines, when used in the therapy of insomnia, is residing in that these substances do alter the compositions of the different sleep stages and the endogenous circadian rhythmicity, with consequences on the organic and psychic sphere which worsen with time.

Sleep is not a non-differentiated homogeneous process. In fact, it consists of different stages which in normal subjects have a precise temporal organization, which has to be respected, in order to grant a sleep as natural as possible; one complete cycle of such stages requires about 90 minutes.

Sleep structure is expressed by two basic situations: the NREM sleep (non-rapid eye movements), subdivided into 4 different stages of increasing depth, and the REM sleep.

The typical sleep architecture is characterized by the recurrent, even if not necessarily hierarchical, succession of NREM stages and by fixed cycles based on the regular alternation between REM and NREM periods.

The organization of sleep into stages and cycles is supplying a structure which can fit to the variable environmental conditions. The different stages of sleep and some of the effects coming from their lacking are reported in table 1 (from Goodman and Gilman, The pharmacological bases of the therapy, 1982, pag. 360).

TABLE 1

| Stage | Effects coming from deprivation |
|---|---|
| 0 (wake) | — |
| 1 (benumbment, sleep is taking place) | The occurrence of the subsequent stages of the sleep is inhibited; no specific symptomatology. |
| 2 (clear sleep condition) | The occurrence of the subsequent stages is inhinbited |
| 3 (transition to deep sleep) | Stage 4 is inhibited |
| 4 ("cerebral" sleep) | Suicidal ideation and diurnal terrors, remarkable rebound phenomena. |
| REM sleep (rapid eye movement) | Anxiety, hyperphagia, behavioural disorders; reduced learning and concentration; hypersexuality, reduced threshold for the evocation of a conclusive outline. |

It is important to evaluate the sleep parameters either during the use of a drug or after its interruption, because, for instance, a too sharp suppression of stage 4 can give rise to the beginning of diurnal terrors or of suicidal ideations and to the transfer to phase (step) 2 of the nightmares usually occurring in the REM phase. Another important parameter to evaluate, as to the sleep quality, is the intrinsic structure of the normal NREM sleep, namely the CAP (cyclic alternating pattern) consisting of periods of encephalographic activity organized in series of biphasic cycles (sleep microstructure) and the CAP-rate, defined as a per cent ratio of the CAP time with respect to thr overall sleep time. The CAP-rate parameter is thus reflecting the "sleep quality". Benzodiazepines markedly reduce the time spent in stages 3 and 4, increase the REM latency time (the time elapsed between a sleep onset and the occurrence of the first REM episode) and moreover reduce, in general, the space occupied by the REM sleep.

It is thus clear that benzodiazepines, although increasing the depth and rest properties of the sleep and the overall length of the sleep, do not respect the physiological composition of the different sleep phases; the chronical treatment by means of such drugs can give rise to very harmful cumulative effects on the usual rythms of sleep wherefrom comes the beginning of unfavourable psychological effects, like for instance increase of the impact of the nightmares, anxiety, irritability, tachycardia, which can vary according to the employed benzodiazepine.

Further drawbacks in the benzodiazepine treatment are evident when the drug administration is interruped after 3 or 4 weeks, and resides in a remarkable rebound effect as to the quantity and intensity of REM sleep, with reduction of the latency time and an overall increase of the time of the REM sleep, which can persist even for a long period.

Such a rebound phenomenon is corresponding to a worsened reappearance of the symptomatology preceding the pharmacological treatment, namely reappearance of anxiety, of insomnia and so on.

At last another undesired effect of benzodiazepines is related to the drug administration in a high dosage or for a prolonged time and resides in the development of tolerance and addiction. These drugs become ineffective when administered for a long time and therefore higher dosages are required in order to achieve the same effects.

The development of tolerance and rebound effects provide anxiety and usually lead to the need of higher and more frequent dosages of drug, thus creating a vicious circle between dosage increase and tolerance, with the conclusive consequence of an alteration of the normal rhythm of the sleep.

Active pharmaceutical compositions, in the treatment of sleep disorders or in the pre-anaesthetic medication, containing melatonin or a derivative thereof, alone or in association with a benzodiazepinic derivative, have never been proposed. In particular are new the pharmaceutical compositions containing melatonin or a derivative thereof, having general formula (I), possibly in association with a benzodiazepinic derivative. In the course of our studies on the activity of melatonin at the level of the central nervous system, we have surprisingly found that melatonin and its derivatives, having general formula (I)

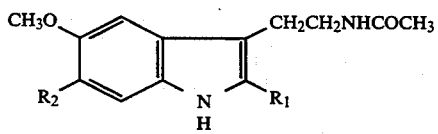

wherein $R_1$ and $R_2$, the same or different, are H or halogens, and in particular three melatonin derivatives, namely 2-iodomelatonin, 2-bromomelatonin and 2-chloromelatonin, can exert a powerful action on the treatment of the sleep disorders and can be advantageously used also in the pre-anaesthesia.

Further, we have surprisingly found that the pharmacological action of benzodiazepines can be considerably increased and that all the undesired effects above can be avoided, by utilizing a pharmaceutical composition according to the present invention, comprising melatonin or a derivative thereof alone or in association with a benzodiazepinic derivative.

The pharmaceutical compositions according to the present invention allow for better results in the treatment of the sleep disorders and in the pre-anaesthetic medication and, when used in association, for lower dosages of benzodiazepines.

The patients taking the pharmaceutical compositions according to the present invention, show a better synchronisation of the diurnal activity, a reduced sleep latency and a longer sleep period; the general conditions, subjectively evaluated by each person, and the "performance status" are considerably improved.

In order to obtain a pharmacological effect which is analogous from the quantitative point of view and definitely better from the qualitative point of view, the pharmaceutical compositions according to the present invention require a lower dosage of the benzodiazepinic component, namely a dosage value between 30 and 60%, with respect to the dosage to be administered when utilizing benzodiazepine alone.

Further, the use of a lower dosage of benzodiazepines can succesfully avoid those undesired effects (alteration of the sleep rithms, rebound effect, development of tolerance) connected to the administration of benzodiazepines in high dosage or for a prolonged periods of time.

Melatonin and its derivatives are further completely devoid of toxicity, even in higher doses, with respect to the dosage to be used in the therapy of sleep disorders.

The pharmaceutical compositions according to the present invention comprise N-acetyl-5-methoxytriptamine (melatonin) or one of its derivatives having general formula (I), preferably 2-iodo-N-acetyl-5-methoxytriptamine (2-iodomelatonin), 2-bromo-N-acetyl-5-methoxytriptamine (2-bromo-melatonin), 2-chloro-N-acetyl-5-methoxytriptamine (2-chloromelatonin) or 6-chloro-N-acetyl-5-methoxytriptamine (6-chloromelatonin), at a dosage comprised between 10 and 100 mg, preferably between 20 and 80 mg, for melatonin, between 10 and 20 mg for 2-iodomelatonin and between 10 and 40 mg for 2-chloromelatonin, 2-bromomelatonin and 6-chloromelatonin, alone or in association with a benzodiazepinic derivative, at a dosage comprised, depending on the used benzodiazepine, between 0.06 and 25 mg.

These pharmaceutical compositions can be administered orally or parenterally and, depending on the desired pharmaceutical form, they will contain all the normally required excipients, commonly used in the pharmacological practice.

The pharmaceutical compositions according to the present invention have to be administered 30–40 minutes before going to bed or before induction of anaesthesia.

In order to show the activity of the compositions according to the present invention, we carried out several tests, taking into consideration different physiological parameters, like, for instance, the data obtained by means of electrocardiogram (ECG) and electroencephalogram (EEG), breathing frequency, objective analysis and personal evaluation.

For exemplification purposes, we report the results of some of the series of performed tests.

Series I

We evaluated the effects of melatonin, 2-iodomelatonin and 2-bromomelatonin on the spontaneous firing activity of single neurons of the parietal cortex of rabbit and of the thalamus nuclei of rat, where we have previously found and described the presence of melatonin receptors.

Materials and methods

Our experimental work was carried out by means of electrophysiological techniques using extracellular registration of single neurons (thalamic or cortical neurons), of the tested animal species (rat and rabbit) anaesthetized by means of urethane or barbiturates. Such recordings were effectuated before, during and after microionophoretic or micropressive application of the substances: by means of multichannel glass microelectrodes. The concentration of the used substances was respectively: Melatonin, 2-bromomelatonin or 2-iodomelatonin ($10^{-6}$–$10^{-7}$M), GABA $10^{-2}$M, Bicuculline $10^{-4}$M. The neurons sensitive to GABA (90% of the studied ones) showed powerful inhibitions when subjected to the GABA action. The basal neuronal activity was taken as 100% and the difference in activity obtained following administration of the tested compounds was evaluated as percent of the basal activity.

The results are reported in Table 2.

TABLE 2

| Active Principle | Administration time (min) | Duration of the effect post-administration (min) | Activity after administration (% basal activity) |
|---|---|---|---|
| Melatonin (100 nM) | 5 | 2.5 | 87 |
| Melatonin (1 μM) | 5 | 4 | 56 |
| GABA (1 mM) | 0.1 | 0.01 | 34 |
| GABA (1 mM) + Melatonin (1 μM) | 0.1 2 | 6 | 20 |
| 2-iodomelatonin (100 nM) | 5 | 5 | 47 |
| GABA (1 mM) + 2-iodomelatonin (100 nM) | 0.1 2 | 7 | 10 |
| 2-bromomelatonin (100 nM) | 5 | 10 | 14 |
| GABA (1 mM) + 2-bromomelatonin (100 nM) | 0.1 2 | 13 | 11 |

*basal activity = 100%

As it clearly results from the data reported in table 2, the administration into the parietal cortex of amounts of the order of nanograms of 2-iodomelatonin and 2-bromomelatonin gave rise to long lasting, powerful inhibitions of the spontaneous activity of both cortical and thalamic neurons.

The administration of melatonin alone, in the same concentration range, gave rise to analogous, though less marked effects, whereas the administration of melatonin and GABA resulted in a considerable inhibition of the spontaneous activity.

GABA is the most common inhibitory neuro transmitter in the central nervous system. The GABA-receptor consists of a macromolecular complex which, besides the sites having strong affinity to the specific transmitter, namely to GABA, possess "modulation" sites where many different substances and molecules are acting.

In general, it is required that the receptor is activated by a previously bound transmitter. Such activation is followed by a series of phenomena which facilitate the binding of the modulating substances. Some molecules, like the ones object of the present invention, as the melatonin halogenated compounds, are showing an "autonomous" (independent) capacity to activate the GABA receptor, which is evident either when the substance is administered alone or in association with GABA itself, whose inhibitory transmitter properties are dramatically augmented by said molecules.

Melatonin, on the contrary, like the benzodiazepines, requires receptor preactivation on the part of GABA.

Either the autonomous mechanisms or the ones dependent on GABA give rise to effects similar to the benzodiazepinic ones, which can be exploited either indipendently or in association with the benzodiazepines themselves.

Series II

We carried out a series of double blind trials, on healthy volunteers, by individually administering in the different sessions, melatonin (MEL, 100 mg per os), Triazolam (TRI, 0.125 mg per os), and melatonin (100 mg per os in association with Triazolam, 0.062 mg per os, MEL+TRI).

The substances under examination were administered at 22.30 h and the polygraphic recording of the sleep parameters was carried out from 23.00 to 07.00 h.

We measured the changes, with respect to the normal reference values (baseline), of 10 fundamental parameters.

The results of such test were recorded on table 3.
The abbreviations used in he table are as follows:
SL: sleep latency
SE: sleep efficiency
WASO: wake after sleep onset
St.: stage (step)
NREM: non rapid eye movement sleep REM: rapid eye movement sleep
CAP: cyclic alternating pattern

TABLE 3

|  | Baseline | MEL | TRI | MEL + TRI |
|---|---|---|---|---|
| Sleep macrostructure |  |  |  |  |
| SL (min) | 5.2 | 5.2 | 3.7* | 6.8 |
| WASO (min) | 18.2 | 9.7* | 5.3* | 11.2* |
| SE (%) | 94.8 | 96.9* | 98.0* | 96.2* |
| Sleep architecture |  |  |  |  |
| St. 1 NREM (%) | 6.1 | 4.4 | 3.3 | 3.4 |
| St. 2 NREM (%) | 53.9 | 52.8 | 49.6 | 51.8 |
| St. 3–4 NREM (%) | 19.6 | 21.5 | 24.6 | 21.8 |
| REM (%) | 20.4 | 21.3 | 22.5 | 23.0 |
| REM Lat. (min) | 99.2 | 85.3 | 83.5 | 86.7 |
| St. shifts/h (n°) | 8.0 | 7.4 | 5.9 | 6.1 |
| Sleep microstructure |  |  |  |  |
| CAP rate (%) | 25.7 | 22.4* | 13.8** | 13.9** |

*$p < 0.05$ vs Baseline
**$p < 0.01$ vs Baseline (ANOVA)

As seen from the data in this table, melatonin administered alone is modifying to a lesser extent the microstructure of sleep, with respect to Triazolam, and it leads therefore to a more natural composition of sleep though it has a limited impact on the microstructure.

The reported data clearly show that 100 mg of melatonin administered in association with half the dosage of triazolam (0.0625 mg) surprisingly produce the same effects as a double dosage (0.125 mg) of Triazolam alone, on the sleep microstructure.

Series III

It is well known that the action of benzodiazepines on healthy subjects is limited and we tested therefore the activity of melatonin agonists in patients suffering from insomnia.

We carried out another series of trials, determining the effects of 2-bromomelatonin administration (2-BrMel) and Triazolam on the sleep parameters in patients suffering from psycho-physiologic insomnia. Twelve patients were successively treated with 2-bromomelatonin (10 mg per os) or triazolam (0.125 mg per os).

Materials and methods

All patients were uniformly selected and classified as suffering from psychophysiological insomnia, according to "The International Classification of Sleep Disorders; Diagnostic and Coding Manual, ASDA, 1990".

The substances were administered at 22.30 h and the polyinsomnographic recording was performed from 23.00 to 07.00 h, by using Medilog 9000 with 8 channel recorder.

The results of this double blind test are reported in table 4.

TABLE 4

|  | Baseline | 2-BrMel | TRI |
|---|---|---|---|
| Sleep macrostructure |  |  |  |
| SL (min) | 20.2 | 19.0 | 19.7 |
| WASO (min) | 61.1 | 42.0* | 51.2* |
| SE (%) | 83.5 | 87.0* | 81.6 |
| WASO (n°) | 15.5 | 11.0* | 11.7* |
| Sleep architecture |  |  |  |
| St. 1 NREM (%) | 6.8 | 6.9 | 5.8 |
| St. 2 NREM (%) | 54.3 | 54.8 | 54.3 |
| St. 3-4 NREM (%) | 16.6 | 16.8 | 16.6 |
| REM (%) | 21.6 | 22.7 | 22.8 |
| REM Lat. (min) | 79.8 | 86.2 | 85.5 |
| REM period (n°) | 4.8 | 4.2 | 5.0 |
| St. shifts/h (n°) | 9.0 | 8.1 | 8.0 |
| Sleep microstructure |  |  |  |
| CAP rate (%) | 43.0 | 32.0* | 28.2* |

*p < 0.05 vs Baseline (Dunnett)

These data clearly show that the administration of only 10 mg of 2-bromomelatonin resulted in significant changes in the basic sleep parameters, that were even more pronounced when compared with the administration of 0.125 mg of Triazolam.

In particular, 2-bromomelatonin proved to be more effective than triazolam regarding some parameters, such as, for instance, "sleep efficiency" and WASO.

We obtained analogous results using 2-iodomelatonin. A very favourable result emerging from these experimental trials is that the sleep architecture was not altered, whereas the efficiency and the quality of sleep were considerably improved. For illustrative and not limiting purposes, we report few pharmaceutical compositions according to the present invention.

EXAMPLE 1

2-bromomelatonin containing capsule
2-bromomelatonin 10 mg
fructose 20 mg

EXAMPLE 2

Melatonin and Triazolam containing capsule
Triazolam 0.0625 mg
melatonin 80 mg
fructose 70 mg

EXAMPLE 3

| Iodomelatonin and Diazepam containing tablet | |
|---|---|
| diazepam | 1 mg |
| iodomelatonin | 20 mg |
| lactose | 73 mg |
| corn starch | 38.3 mg |
| polyvinylpyrrolidone 25000 | 4 mg |
| magnesium stearate | 0.3 mg |
| hydroxypropylmethylcellulose | 1 mg |

EXAMPLE 4

| Capsule containing melatonin and flurazepam hydrochloride | |
|---|---|
| flurazepam hydrochloride | 7 mg |
| melatonin | 60 mg |
| lactose | 120 mg |
| talc | 6 mg |
| magnesium stearate | 4 mg |

EXAMPLE 5

| Soft gelatine capsule | |
|---|---|
| 2-bromomelatonin | 10 mg |
| polyethylene glycol 400 (50% solution) | 200 µl |

We claim:

1. Pharmaceutical compositions active in the therapy of sleep disorders and in the preanaesthetic medication, comprising therapeutically effective amounts of melatonin or of a derivative thereof having general formula (I)

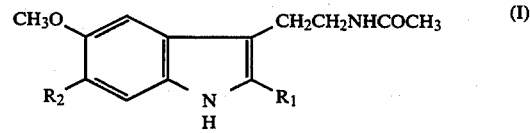

wherein $R_1$ and $R_2$, are the same or different, are H or halogen, in association with a benzodiazepine derivative which acts on the central nervous system through receptors of gamma amino-butyric acid and with suitable excipients.

2. Pharmaceutical compositions according to claim 1, characterized in that the therapeutically effective amount of melatonin or of its derivatives is comprised between 10 and 100 mg and as to the benzodiazepinic derivative is comprised between 0.06 and 25 mg.

3. Pharmaceutical compositions according to claim 2, characterized in that the therapeutically effective amount of melatonin is comprised between 20 and 80 mg.

4. Pharmaceutical compositions according to claim 1, characterized in that the melatonin derivative is 2-iodomelatonin.

5. Pharmaceutical compositions according to claim 4, characterized in that the therapeutically effective amount is comprised between 10 and 20 mg.

6. Pharmaceutical compositions according to claim 1, characterized in that the melatonin derivative is 6-chloromelatonin.

7. Pharmaceutical compositions according to claim 6, characterized in that the therapeutical effective amount is comprised between 10 and 40 mg.

8. Pharmaceutical compositions according to claim 1, characterized in that the melatonin derivative is 2-bromomelatonin.

9. Pharmaceutical compositions according to claim 8, characterized in that the therapeutical effective amount is comprised between 10 and 40 mg.

10. Pharmaceutical compositions according to claim 1, characterized in that the melatonin derivative is 2-chloromelatonin.

11. Pharmaceutical compositions according to claim 10, characterized in that the therapeutical effective amount is comprised between 10 and 40 mg.

12. Pharmaceutical compositions according to claim 1 wherein the amount of the benzodiazepine is 30–60% of the normal therapeutic dose.

13. A method of reducing the CAP rate during sleep which comprises administering an effective amount of a composition of claim 1.

14. A method as defined in claim 13 wherein the composition comprises 100 mg of melatonin and 0.0625 mg of triazolam.

15. Therapeutical method for the treatment of sleep disorders characterized by the administration of a pharmaceutical composition comprising therapeutically effective amounts of melatonin having general formula (I).

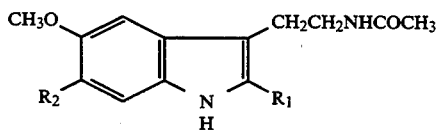

wherein $R_1$ and $R_2$, are H and a benzodiazepine derivative which acts on the central nervous system through receptors of gamma amino-butyric acid.

16. Therapeutical method according to claim 15, characterized in that the therapeutically effective amount of melatonin is comprised between 10 and 100 mg and the amount of the benzodiazepine derivative which acts on the central nervous system through receptors of gamma amino-butyric acid is comprised between 0.06 and 25 mg.

17. Therapeutical method according to claim 16, characterized in that the therapeutically effective amount of melatonin is comprised between 20 and 80 mg.

18. Therapeutical method according to claim 15 wherein the composition is administered orally and comprises 100 mg of melatonin and 0.0625 mg of triazolam.

19. Therapeutical method according to claim 15 wherein the composition is administered orally and comprises 7 mg of flurazepam hydrochoride and 60 mg of melatonin.

20. Therapeutical method according to claim 15 where the amount of the benzodiazepine is 30–60% of the normal therapeutic dose.

21. Therapeutical method for the treatment of sleep disorders characterized by the administration of a pharmaceutical composition comprising therapeutically effective amounts of a melatonin derivative having the general formula:

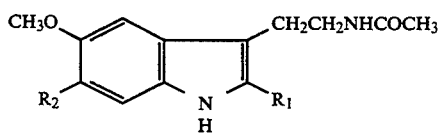

wherein at least one of $R_1$ and $R_2$ is halogen.

22. Therapeutical method according to claim 21, characterized in that the melatonin derivative is 2-iodomelatonin.

23. Therapeutical method according to claim 22, characterized in that the therapeutically effective amount is comprised between 10 and 20 mg.

24. Therapeutical method according to claim 21, characterized in that the melatonin derivative is 2-chloromelatonin.

25. Therapeutical method according to claim 24, characterized in that the therapeutically effective amount is comprised between 10 and 40 mg.

26. Therapeutical method according to claim 21, characterized in that the melatonin derivative is 6-chloromelatonin.

27. Therapeutical method according to claim 26, characterized in that the therapeutically effective amount is comprised between 10 and 40 mg.

28. Therapeutical method according to claim 21, characterized in that the melatonin derivative is 2-bromomelatonin.

29. Therapeutical method according to claim 28, characterized in that the therapeutically effective amount is comprised between 10 and 40 mg.

30. Therapeutical method according to claim 21 wherein the composition is administered orally and comprises 1 mg of diazepam and 20 mg of iodomelatonin.

* * * * *